United States Patent [19]

Seng et al.

[11] Patent Number: 4,695,652

[45] Date of Patent: Sep. 22, 1987

[54] PROCESS FOR THE PREPARATION OF β-AMINOETHYL KETONES

[75] Inventors: Florin Seng, Bergisch-Gladbach; Josef Bremen, Leverkusen, both of Fed. Rep. of Germany

[73] Assignee: Bayer Aktiengesellschaft, Leverkusen, Fed. Rep. of Germany

[21] Appl. No.: 783,462

[22] Filed: Oct. 2, 1985

[30] Foreign Application Priority Data

Oct. 5, 1984 [DE] Fed. Rep. of Germany ....... 3436450

[51] Int. Cl.$^4$ ..................... C07C 97/10; C07C 85/18
[52] U.S. Cl. .................................... 564/343; 544/175; 546/237
[58] Field of Search ......................... 546/237; 544/175; 564/337, 342, 345, 343

[56] References Cited

U.S. PATENT DOCUMENTS

| | | | |
|---|---|---|---|
| 2,186,929 | 12/1957 | Lobby | 564/343 |
| 2,861,993 | 11/1958 | Schlichting et al. | 546/237 X |
| 3,133,080 | 5/1964 | Sarkar et al. | 260/239.9 |
| 4,181,803 | 1/1980 | Marita et al. | 546/237 |

OTHER PUBLICATIONS

Hackh's Chemical Dictionary, Fourth Ed., p. 311.
Houben–Weyl, *Methoden der Organischen Chemie*, XI/1, pp. 731–793 (1957).
Chemie Lexikon, Romp, pp. 3095–3096.
The Van Nostrand Chemist's Dictionary, 1954, Mannich Reaction, p. 450.
Hackh's Chemical Dictionary, Fourth Edition, Mannich Reaction, p. 408.

*Primary Examiner*—Charles F. Warren
*Assistant Examiner*—Carolyn S. Greason
*Attorney, Agent, or Firm*—Sprung Horn Kramer & Woods

[57] ABSTRACT

β-Aminoethyl ketones are obtained in a low-polluting manner by Mannich condensation of an aryl ketone having an acidic H with an aldehyde and ammonia or an amine by carrying out the reaction in organic nitriles in the presence of a sulphonic acid or in gycol either in the presence of a sulphonic acid or sulphuric acid.

6 Claims, No Drawings

PROCESS FOR THE PREPARATION OF β-AMINOETHYL KETONES

The invention relates to a process for the preparation of β-aminoethyl ketones by condensation of acidic aryl ketones having an acid H with aldehydes and ammonia or amines in the sense of a "Mannich reaction".

It is generally known (compare, for example, "Synthesis" 1973, 703 et seq. and "Houben-Weyl" 11/I (1957), 731 et seq.), that this condensation is carried out in the presence of hydrochloric acid in an aqueous or (aqueous)-alcoholic medium, the acid advantageously being employed in the form of the hydrochlorides of the amines used as reactants.

This method, which has proved itself per se, has the disadvantage that very toxic chloromethyl ether can be formed as a by-product.

It is furthermore known that the aromatic β-aminoketones can also be prepared by reacting the corresponding β-halogeno-ketones with amines.

This process is also not optimum, since the β-halogeno-ketones employed as the starting material can lead to skin irritations and allergies.

The object of the present invention was therefore to provide a process which does not have the abovementioned disadvantages.

According to the invention, this object is achieved by carrying out the Mannich condensation in organic nitriles or glycol ethers in the presence of sulphonic acids or, in the case of the glycol ethers, also in the presence of sulphuric acid.

It must be regarded as decidedly surprising that the reaction also proceeds very smoothly under these conditions and gives good yields, since the acid catalysts to be employed according to the invention fail in the usual aqueous-alcoholic solvents.

The new process is particularly suitable for the preparation of compounds of the formula

wherein
Ar denotes an aryl radical,
R denotes hydrogen, alkyl, aralkyl or cycloalkyl,
R' denotes OH, alkyl or aryl and
n denotes the number 1 or 2,
with the proviso that R represents alkyl or two radicals R, together with the N atom, form the remaining members of a saturated heterocyclic radical if n denotes the number 1.

Suitable radicals Ar are carbocyclic aromatic radicals, such as, for example, those of the naphthalene and benzene series. Phenyl radicals, which are optionally substituted, for example by Cl, —CH₃ or -phenyl, are preferred.

Suitable alkyl radicals R/R' are those with 1-6 C atoms, which can also be substituted, for example by —OH or —OC₁-C₄-alkyl.

Suitable aralkyl radicals are benzyl and phenethyl.
Suitable cycloalkyl radicals are cyclohexyl radicals.
Suitable aryl radicals R' are phenyl radicals which are optionally substituted by CH₃ or Cl.
Suitable heterocyclic radicals which two radicals can form are:

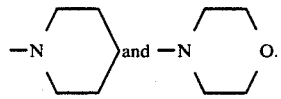

The process according to the invention is otherwise carried out under the customary conditions of a Mannich reaction.

The preferred aldehyde to be employed is formaldehyde. Examples of suitable amines are: methyl-, ethyl-, n-propyl-, dimethyl-, diethyl- and cyclohexyl-amine, and piperidine and morpholine.

Examples of solvents which may be mentioned are: acetonitrile, propionitrile, glycol monomethyl ether and propylene glycol monomethyl ether.

The reaction temperatures are in general in the range between 80° and 130° C.

Preferred sulphonic acids are methane-, benzene- and p-toluene-sulphonic acid.

At least 1 mole of the acid catalysts (that is to say either sulphuric acid or the sulphonic acids), are employed per mole of amine, care being taken that the catalyst and amine are first brought into contact before the other reactants are added. The corresponding amine salts are therefore advantageously used, as in the classical Mannich reaction.

Most of the bases on which the process products of the abovementioned formula are based are known, and they are useful intermediates for the preparation of optical brighteners of the pyrazoline type (compare, for example, U.S. Pat. No. 3,133,080).

EXAMPLE 1

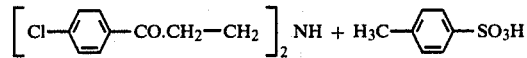

30.9 g (0.2 mole) of 4-chloroacetophenone are introduced into 50 ml of acetonitrile. 13.6 g (0.2 mole) of 25% strength aqueous ammonia and 57 g (0.3 mole) of p-toluenesulphonic acid are added and the mixture is stirred for 15 minutes. Thereafter, 6 g (0.2 mole) of paraformaldehyde are added and the mixture is stirred at 80° C. for 10 hours. On subsequent cooling to 0° C., 51 g of crude product precipitate. 42 g (80% of theory) of bis-[β-4-chlorobenzoyl-ethyl]-ammonium toluene sulphonate of melting point 190°–191° C. are obtained by extraction by stirring in 200 ml of acetone.

The following compounds are obtained analogously:

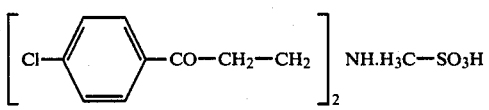

(2)

-continued
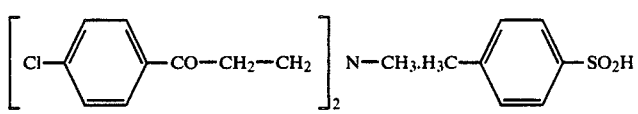 (3)
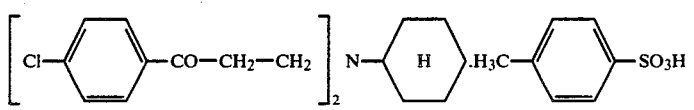 (4)
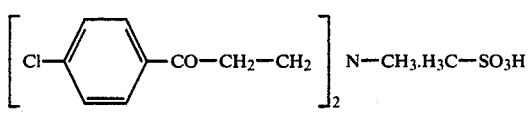 (5)
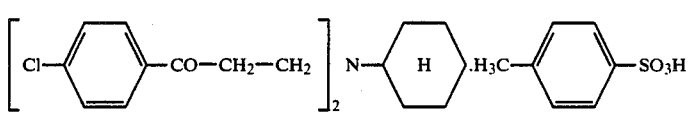 (6)
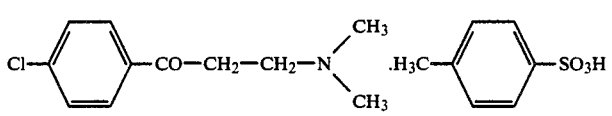 (7)
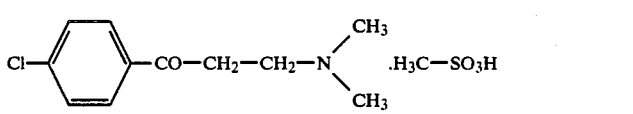 (8)
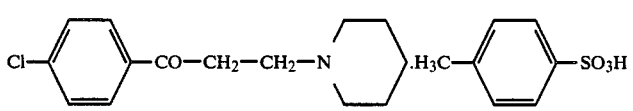 (9)
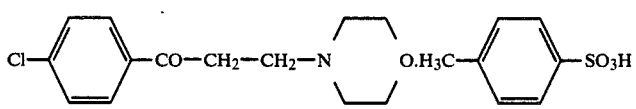 (10)
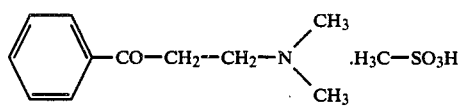 (11)
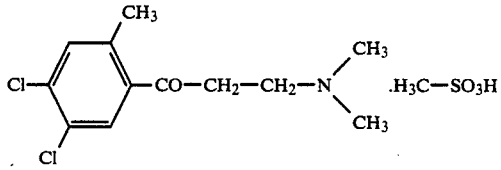 (12)
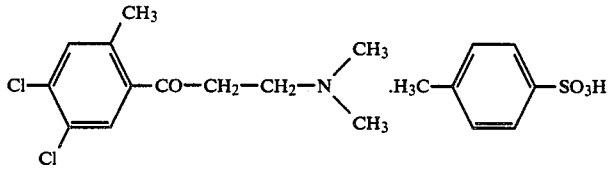 (13)
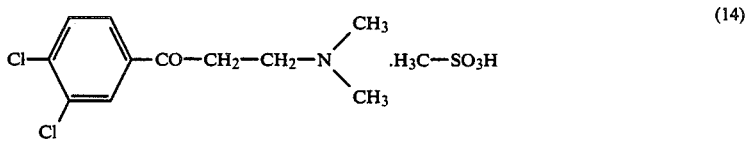 (14)

EXAMPLE 15

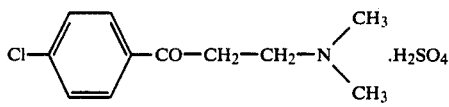

309 g (2 moles) of 4-chloracetophenone are introduced into 300 ml of propylene glycol monomethyl ether. 520 g (5.2 moles) of concentrated sulphuric acid and 468 g (5.2 moles) of 50% strength aqueous dimethylamine solution are added and the mixture is stirred for 15 minutes.

Thereafter, 78 g (2.6 moles) of paraformaldehyde are added and the mixture is stirred at 110°–120° C. for 3 hours.

The solvent is then distilled off under a water pump vacuum and the solid residue which remains is stirred into 1 l of acetone. 468 g of β-4-chlorobenzoyl-ethyl-dimethylammonium sulphate of melting point 120°–122° C. are obtained. A further 100 g of product of melting point 118°–120° C. separate out of the filtrate when this is left to stand overnight.

We claim:

1. In a process for the preparation of a β-aminoethyl ketone by the condensation of a methyl aryl ketone with an aldehyde and ammonia or an amine, the improvement comprising carrying out the reaction in the absence of hydrochloric acid or hydrochlorides and in the presence of an organic nitrile and a sulphonic acid or in the presence of a glycol ether sulphuric acid.

2. A process according to claim 1, wherein the ammonia or the amine is employed in the form of the sulphuric acid or sulphonic acid salt.

3. A process according to claim 1, wherein the reaction is carried out in the presence of acetonitrile or propylene glycol monomethyl ether.

4. A process according to claim 1, wherein formaldehyde is employed as the aldehyde.

5. A process according to claim 1, wherein benzene-, p-toluene- or methane-sulphonic acid is employed as the sulphonic acid.

6. A process according to claim 1, wherein the reaction is carried out in the presence of a mixture of 1 mole of free amine or ammonia to at least one mole of sulphuric acid or sulphonic acid.

* * * * *